US011213228B2

(12) United States Patent
Galano

(10) Patent No.: US 11,213,228 B2
(45) Date of Patent: Jan. 4, 2022

(54) STACKED SENSOR ASSEMBLY FOR FLUID ANALYZER

(71) Applicant: Siemens Healthcare Diagnostics Inc., Tarrytown, NY (US)

(72) Inventor: Kenneth P. Galano, Wrentham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/973,921

(22) PCT Filed: Jun. 20, 2019

(86) PCT No.: PCT/US2019/038135
§ 371 (c)(1),
(2) Date: Dec. 10, 2020

(87) PCT Pub. No.: WO2020/005683
PCT Pub. Date: Jan. 2, 2020

(65) Prior Publication Data
US 2021/0244322 A1 Aug. 12, 2021

Related U.S. Application Data

(60) Provisional application No. 62/692,053, filed on Jun. 29, 2018.

(51) Int. Cl.
*B01L 3/00* (2006.01)
*C12Q 1/00* (2006.01)
(Continued)

(52) U.S. Cl.
CPC ........ *A61B 5/14552* (2013.01); *A61B 5/1468* (2013.01); *A61B 5/1486* (2013.01);
(Continued)

(58) Field of Classification Search
CPC ........ B01L 3/502707; B01L 3/502715; B01L 3/5027; B01L 3/502; B01L 3/50;
(Continued)

(56) References Cited

U.S. PATENT DOCUMENTS 6,123,820 A 9/2000 Bergkuist et al.
2011/0076690 A1 3/2011 Gumbrecht et al.
(Continued)

OTHER PUBLICATIONS

International Search Report and Written Opinion of International Application No. PCT/US2019/038135 dated Aug. 29, 2019.
(Continued)

*Primary Examiner* — Christine T Mui
(74) *Attorney, Agent, or Firm* — Dunlap Codding, P.C.

(57) ABSTRACT

A sensor assembly for analysis of physical parameters and chemical constituents of small volume samples of bodily fluids with at least two analyte sensors. The sensor assembly including a separation panel with an upper surface and a lower surface and upper and lower fluid channels disposed within the upper and lower surfaces respectively. The fluid channels extending substantially between the first and second ends and when in an operating mode bodily fluid is in fluid communication with both the upper and lower fluid channels. The sensor assembly including a potentiometric chip positioned atop and an amperometric chip positioned beneath the separation panel with at least one analyte sensor positioned above and beneath each of the fluid channels and when the sensor assembly is in an operating mode the fluid is in fluid communication with the analyte sensors. A bonding media is disposed beneath the amperometric chip.

22 Claims, 7 Drawing Sheets

(51) Int. Cl.
  *A61B 5/1455* (2006.01)
  *A61B 5/145* (2006.01)
  *A61B 5/1468* (2006.01)
  *A61B 5/1486* (2006.01)
  *G01N 27/327* (2006.01)
  *G01N 33/49* (2006.01)
(52) U.S. Cl.
  CPC ...... *A61B 5/14532* (2013.01); *A61B 5/14535* (2013.01); *A61B 5/14546* (2013.01); *B01L 3/502707* (2013.01); *B01L 3/502715* (2013.01); *C12Q 1/006* (2013.01); *G01N 27/3271* (2013.01); *G01N 33/49* (2013.01); *A61B 2562/063* (2013.01); *A61B 2562/12* (2013.01); *B01L 2200/0689* (2013.01); *B01L 2300/0636* (2013.01); *B01L 2300/0861* (2013.01)
(58) Field of Classification Search
  CPC ......... B01L 2200/0689; B01L 2200/06; B01L 2300/0636; B01L 2300/0861; G01N 33/49; G01N 27/3271

USPC .................................................. 422/68.1, 50
See application file for complete search history.

(56) References Cited

U.S. PATENT DOCUMENTS

| | | |
|---|---|---|
| 2014/0378341 A1 | 12/2014 | Glezer et al. |
| 2016/0216284 A1 | 7/2016 | Misener et al. |
| 2017/0069555 A1* | 3/2017 | Milaninia ............... H01L 23/04 |
| 2017/0074870 A1 | 3/2017 | Konry et al. |
| 2017/0172484 A1 | 6/2017 | Sonner et al. |

OTHER PUBLICATIONS

European Search Report and Search Opinion of European Application No. 19827142.1 dated Jul. 15, 2021.

* cited by examiner

STACKED SENSOR ASSEMBLY FOR FLUID ANALYZER

The subject application claims benefit under 35 USC § 119(e) of US provisional Application No. 62/692,053, filed Jun. 29, 2018. The entire contents of the above-referenced patent application are hereby expressly incorporated herein by reference.

FIELD OF THE DISCLOSURE

The disclosure herein relates generally to the field of sensors used in the analysis of fluid properties. The disclosed sensor assembly is embodied in a sensor cartridge which is especially adapted for use in biomedical applications so as to assist in the analysis of multiple physical parameters and/or chemical constituents of small volume samples of bodily fluids such as whole blood.

BACKGROUND

In a variety of instances it is desirable to measure the constituents in a bodily fluid to include, for example, partial pressure of blood gasses in a whole blood sample, concentrations of electrolytes in the blood sample, and the hematocrit value of the blood sample. For example, measuring $pCO_2$, $pO_2$, pH, $Na^+$, $K^+$, $Ca^{2+}$ and hematocrit value are primary clinical indications in assessing the condition of a medical patient. In addition, in an attempt to use as little of the patient's blood as possible in each analysis performed, the devices which are employed to analyze a blood sample are preferably relatively small. Performing blood analysis using a small blood sample is important, for example, when a relatively large number of samples must be taken in a relatively short amount of time or if the volume of blood is limited, as in neonates.

For example, patients in intensive care may require a sampling frequency of 15-20 per day for blood gas and clinical chemistry measurements, leading to a potentially large loss of blood during patient assessment. In addition, by reducing the size of the analyzer sufficiently to make the unit portable, analysis can be performed at the point of care. Also, reduced size typically means reduced turnaround time. Furthermore, in order to limit the number of tests which must be performed it is desirable to gather as much information as possible upon completion of each test. However, size limitations are imposed upon the sensors that are used to measure blood chemistry. These size limitations are in large part due to physical geometries of the sensors and the connections to the sensors.

Point of care blood gas analyzers permit in vitro analysis at the patient's bedside, in the emergency room, or in the intensive care unit. These units use solid state sensors with thin-film electrodes. The microchips, reagents, calibrators, and a sampling device are all contained within a disposable cartridge system. Healthcare facilities can select cartridges with additional test options, including potassium, glucose, BUN and lactate. Because whole blood can be tested, minimal specimen processing is needed; the sample does not have to be centrifuged and the plasma separated from the red blood cells prior to testing.

In settings with medium-to high volume sample testing, a multi-use cartridge system is used. These cartridges can be customized to the specific analyte menu and to the volume of testing. The number of samples measured on a cartridge may vary from 25 to 750 and once loaded into the analyzer, the cartridge typically has an in-use life of between 14 and 30 days.

The basic principle of operation for blood gas analyzers has not changed significantly from earlier units. In about 2005 self-contained cartridges were introduced into several analytical systems, paving the way for point of care testing and compact units. Whole blood can be analyzed for many analytes, including the electrolytes potassium ($K^+$), sodium ($Na^+$), and calcium ($Ca^{2+}$) and metabolites such as glucose, lactate, blood urea nitrogen (BUN), and creatine. The sensors used for these measurements are ion-specific or ion-selective electrodes (ISE). These sensors are membrane-based electrochemical transducers that respond to a specific ion. Biosensors are used in analyzers in the traditional clinical laboratory, but also in point-of-care testing devices. Biosensors convert the biochemical signal into an electrical signal.

Electrolytes are determined by potentiometric measurements, a form of electrochemical analysis. In potentiometry, the potential or voltage is measured between the two electrodes in a solution. These potentials can also be produced when a metal and ions of that metal are present in a solution. By using a membrane that is semipermeable to the ion, different concentrations of the ion can be separated. These systems use a reference and a measuring electrode. A constant voltage is applied to the reference electrode; the difference in voltage between the reference and measuring electrode is used to calculate the concentration of the ion in solution.

Ion-selective electrodes are based on a modification of the principle of potentiometry. The potential difference or electron flow is created by selectively transferring the ion to be measured from the sample solution to the membrane phase. The ion-selective electrode measures the free ion concentration of the desired analyte on a selectively produced membrane. Membranes have a complex composition and contain organic solvents, inert polymers, plasticizers, and ionophores wherein the ionophores are molecules that increase the membrane's permeability to the specific ion.

Amperometric methods measure the current flow produced from oxidation-reduction reactions. Types of amperometry include enzyme electrodes, such as the glucose oxidase method and the Clark $pO_2$ electrode. These types of designs are well known as biosensors and are adaptable for testing in the clinical laboratory as well as for point of care testing. Enzyme-based biosensor technology was first developed to measure blood glucose. A solution of glucose oxidase is placed between the gas permeable membrane of the $pO_2$ electrode and an outer membrane that is semipermeable. Glucose in the blood diffuses through the semipermeable membrane and reacts with the glucose oxidase. Glucose is converted by glucose oxidase to hydrogen peroxide and gluconic acid.

A polarizing voltage is applied to the electrode, which oxidizes the hydrogen peroxide and contributes to the loss of electrons. Oxygen is consumed near the surface of the $pO_2$ electrode and its rate of consumption is measured. The loss of electrons and rate of decrease of $pO_2$ is directly proportional to the glucose concentration in the sample. Enzyme-based biosensors are also used to measure cholesterol, creatine, and pyruvate.

The basic principles of operation for laboratory blood gas analyzers are the same as for the previously described electrodes for pH, $pCO_2$, and $pO_2$; and ion specific electrodes for the measurement of electrolytes. Approximately 50-120 µl of a well-mixed arterial blood sample are typically injected through the inlet and sample probe into the measuring chamber. The specimen then contacts the surface of each electrode for several seconds.

One of the principal challenges with existing sensor assemblies is that performing blood analysis using a small blood sample is important when a relatively large number of samples must be taken in a relatively short amount of time or if the volume of blood is limited, as in neonates.

Accordingly, it would be desirable to provide a sensor assembly which remains accurate over a relatively long period of exposure to electrolytes and blood samples, uses a very small sample size, and detects the concentration of a number of different electrolytes as well as the partial pressure of a number of blood gases all in a single analysis.

SUMMARY

Heel sticks and draws from arterial lines are the most commonly used sites for blood draws. Heel sticks require a high degree of technical expertise to be done properly and without inflicting unnecessary pain or harm to the patient. Frequent blood draws for laboratory testing create the risk of iatrogenic anemia. It has been estimated that 64% of infants <1500 g receive transfusions for anemia due in part to frequent or excessive blood draws. With a plasma volume of 4-5% of body weight, a 1,500 g infant has a total of 70 mL of plasma. Blood transfusion may be required when 10% or more of a neonate's blood volume is withdrawn in 2-3 days. This amount represents about 80 mL/kg of body weight for a full-term infant, and about 100 mL/kg for a preterm infant.

The volume and number of blood draws have been reduced in recent years due to transcutaneous monitoring and newer equipment. Minimizing the volume of blood draws reduces the subsequent need for transfusion as well as the risk associated with transfusion. Many of the current clinical chemistry analyzers require small blood sample volumes for testing, with many sensor arrays requiring between 45 μL to 400 μL, depending on the number of analytes being measured (e.g., blood gases, electrolytes, etc.). The hematocrit of an infant can be >60%, reducing the volume of serum or plasma in the collection container. The "dead volume", consisting of the volume of specimen that must be in the instrument's sampling container, is required in addition to the specimen volume and must be minimal for neonatal applications.

The sensor array disclosed herein requires a sample volume of no greater than 30 μL+/−1 μl in order to pass a sufficient quantity of fluid past each of the analyte sensors. The sensor assembly is capable of supporting numerous analyte sensors with the sensor assembly including a molded separation panel, a potentiometric chip disposed atop the separation panel, an amperometric chip disposed beneath the separation panel, and a bonding media disposed beneath the amperometric chip. The separation panel includes an upper surface and a lower surface and first and second longitudinally disposed ends.

A fluid channel is molded into the upper surface and spans substantially between the first and second longitudinally disposed ends. A second fluid channel is molded into the lower molded surface and spans substantially between the first and second longitudinally disposed ends. The first and second fluid channels have a total volume of 30 μl+/−1 μl. Analyte sensors are strategically located above and below the upper and lower fluid chambers to quantify the concentration or pressure of the constituents of interest.

It is an object of the sensor assembly disclosed herein to provide a low cost disposable sensor assembly.

It is a further object of the sensor assembly disclosed herein to compactly provide a disposable sensor assembly capable of housing a large number of analyte sensors.

It is a further object of the sensor assembly disclosed herein to provide a sensor assembly that requires a blood volume of no greater than 30 μL.

These, together with other aspects of the disclosed sensor array, along with the various features of novelty that characterize the technology, are pointed out with particularity in the claims annexed hereto and form a part of this disclosed technology. For a better understanding of the disclosed technology, its operating advantages and the specific objects attained by its uses, reference should be made to the accompanying drawings and descriptive matter in which there are illustrated exemplary embodiments of the disclosed technology.

BRIEF DESCRIPTION OF THE DRAWINGS

Illustrative embodiments of the disclosed technology are described in detail below with reference to the attached drawing figures, which are incorporated by reference herein and wherein.

DETAILED DESCRIPTION

Disclosed herein is a stacked sensor assembly 10 for determining partial pressures of gases, concentrations of electrolytes and metabolites in a fluid sample. The stacked sensor configuration is ideal for minimizing the surface area required for the sensor assembly without sacrificing the functionality of the sensor assembly. In clinical laboratory settings where available space may be at a premium due to the large number of instruments utilized, this stacked sensor configuration offers an attractive option for reducing the footprint of the sensor assembly. Fluids, such as whole blood, can be analyzed for many analytes, including the electrolytes potassium ($K^+$), sodium ($Na^+$), and calcium ($Ca^{2+}$) and metabolites such as glucose, lactate, blood urea nitrogen (BUN), and creatine. The sensors used for these measurements are ion-specific or ion-selective electrodes (ISE).

Figure 1:
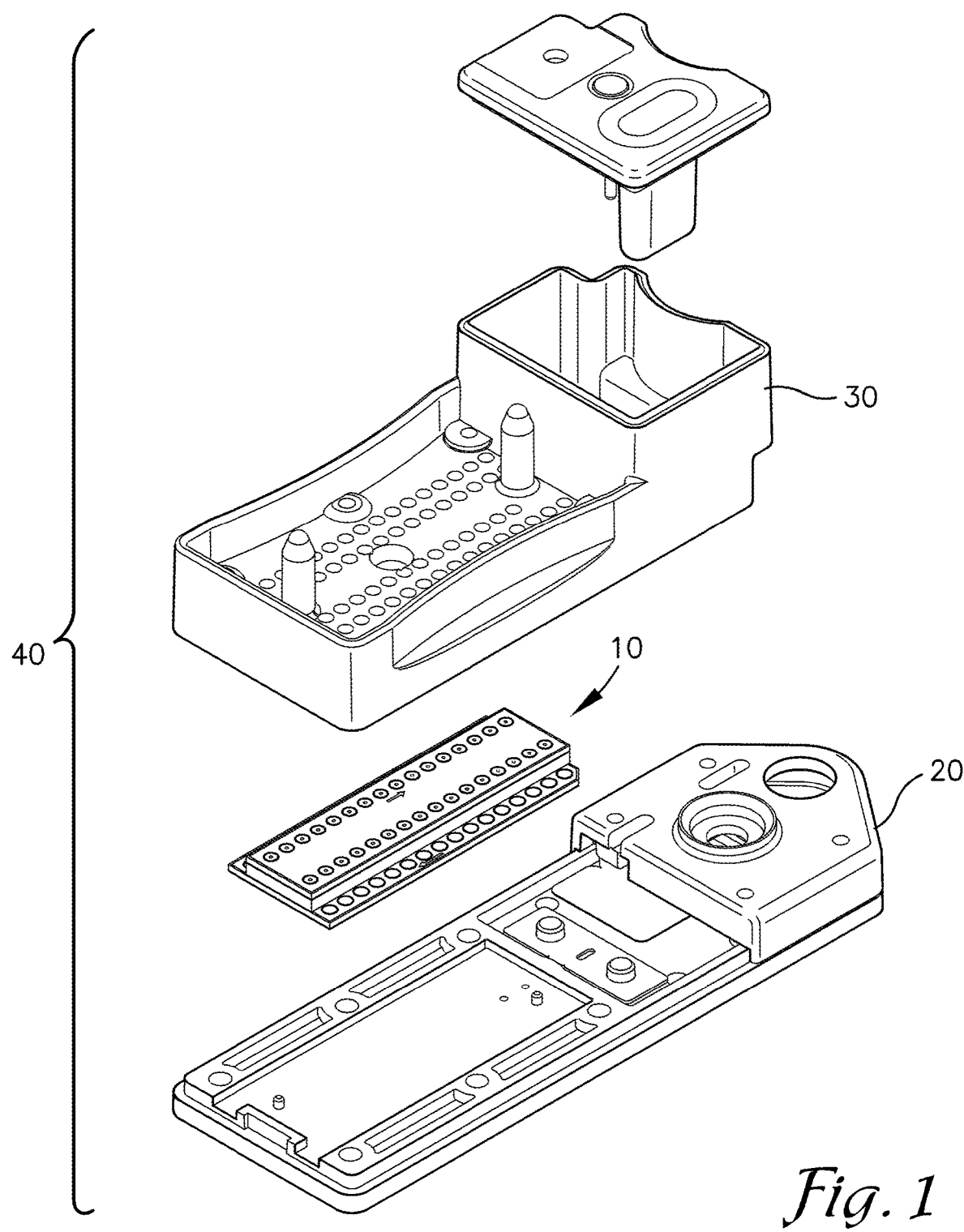
FIG. 1 is a perspective view of an embodiment of an exploded cartridge with case and cover and including an embodiment of a sensor assembly.

An embodiment of the stacked sensor assembly 10 disclosed herein is depicted in FIG. 1. The stacked sensor assembly 10 is shown ready for loading onto the cartridge base 20 and the cartridge cover 30 located atop the stacked sensor assembly 10. The fully assembled cartridge 40 includes the stacked sensor assembly 10 as well as the cartridge base 20 and the cartridge cover 30. The cartridge 40 is sold as a unit for installation in a fluid gas analyzer, such as a blood gas analyzer, that is well known in the industry and sold by several manufacturers.

Figure 2:
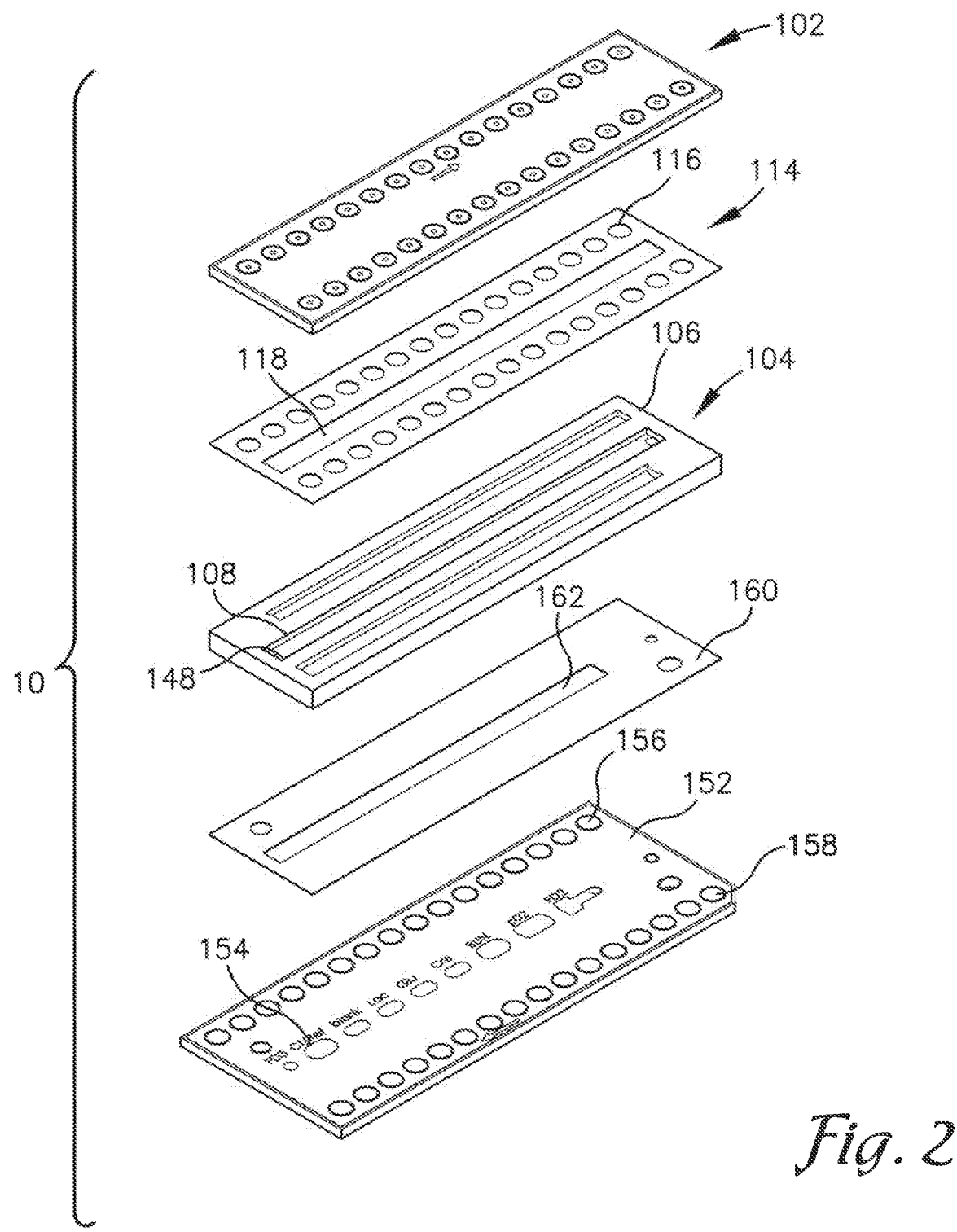
FIG. 2 is an exploded topside view of an embodiment of the sensor assembly components.

As shown in FIG. 2, the stacked sensor assembly 10 is comprised of multiple layers. The uppermost layer may be comprised of solely a potentiometric chip 102 or a combination of potentiometric sensors and other types of sensors. The discussion below details the utilization of potentiometric and amperometric chip sets; however, it should be understood that the disclosure herein contemplates the combination of many types of sensors to include potentiometric, and amperometric, sensors on each chip. The potentiometric chip 102 operates pursuant to a form of electrochemical analysis. In potentiometry, the potential or voltage is measured between the two electrodes in a solution. These potentials can also be produced when a metal and ions of that metal are present in a solution. By using a membrane that is semipermeable to the ion, different concentrations of the ion can be separated. These systems use a reference and a measuring electrode as is well understood by those skilled in the art. A constant voltage is applied to the reference electrode; the difference in voltage between the reference and measuring electrode is used to calculate the concentration of the ion in solution.

Ion-selective electrodes are based on a modification of the principle of potentiometry. The potential difference or electron flow is created by selectively transferring the ion to be measured from the sample solution to the membrane phase. The ion-selective electrode measures the free ion concentration of the desired analyte on a selectively produced membrane. Membranes have a complex composition and contain organic solvents, inert polymers, plasticizers, and ionophores wherein the ionophores are molecules that increase the membrane's permeability to the specific ion.

Figure 3:
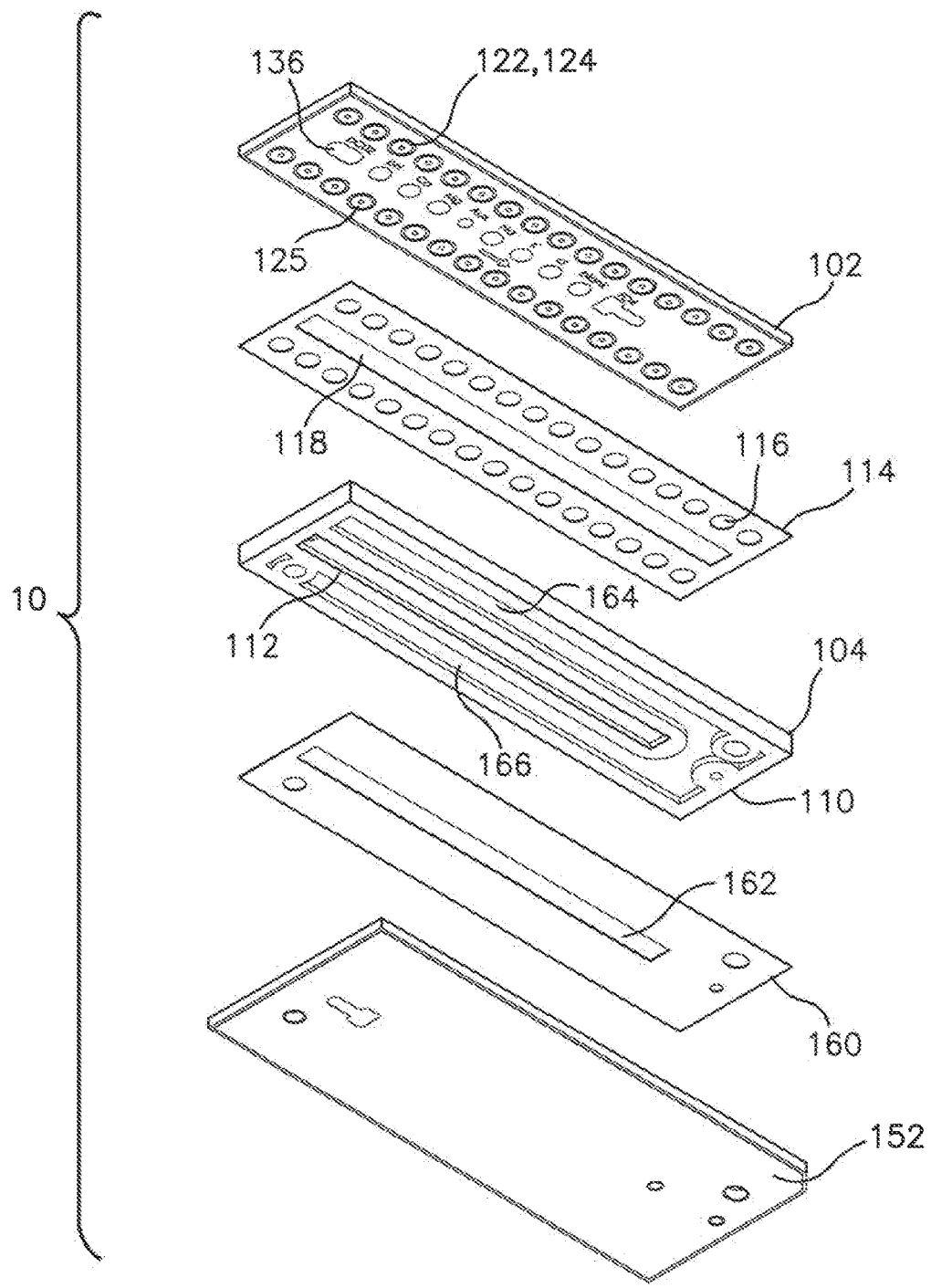
FIG. 3 is an exploded bottom side view of an embodiment of the sensor assembly components.

As seen in FIG. 2, disposed beneath the potentiometric chip 102 is the separation panel 104. The separation panel 104 includes an upper surface 106 with an upper fluid channel 108 for passage there through of the sample fluid. The separation panel 104 also reduces the potential for unintended electromagnetic cross-talk between sensors located on the oppositely disposed chip thereby improving the accuracy and reliability of the sensor data. As seen in FIG. 3, the separation panel 104 includes a lower surface 110 with a lower fluid channel 112. The lower fluid channel 112 is in fluid communication with the upper fluid channel 108, as will be discussed in greater detail below. Optionally disposed between the potentiometric chip 102 and the separation panel 104 may be an upper gasket 114. The upper gasket 114 seals the separation panel 104 against leakage of the sample fluid and is preferably comprised of a flexible fluid resistant material capable of forming a seal against leakage. The upper gasket 114 may include a series of perforations 116 located on each side of a centralized cutout 118. The perforations 116 in the upper gasket 114 may provide an opening for the lower protruding surface 122 of the analyte sensor contact points 124, 125.

As previously discussed, the potentiometric chip 102 is positioned atop the separation panel 104 and includes, as shown in FIG. 3, at least one analyte sensor 136, and preferably many more are positioned over the upper fluid channel 108. Each analyte sensor 136 includes two electrical contact points 124, 125 for connecting the analyte sensor 136 to an analyzer (not shown).

Figure 4:
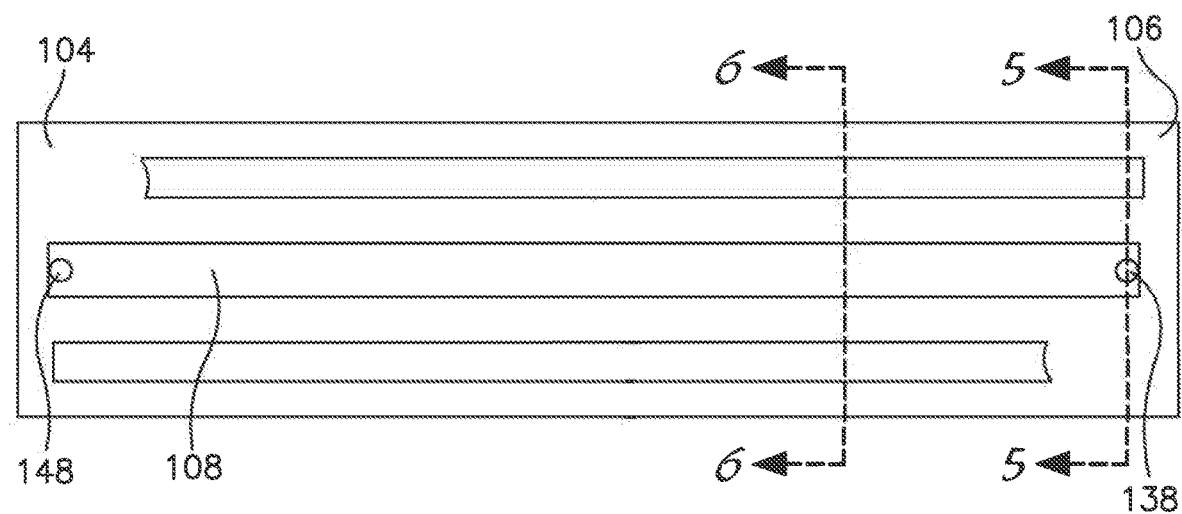
FIG. 4 is a plan view of an embodiment of a separation panel of the sensor assembly disclosed herein.
Figure 5:
FIG. 5 is a cross-sectional view of the separation panel of FIG. 4 taken along line 5-5.
Figure 6:
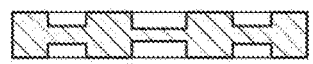
FIG. 6 is a cross-sectional view of the separation panel of FIG. 4 taken along line 6-6.

The upper fluid channel 108 serves as a conduit for the fluid being measured by an upper analyte sensor 136. This fluid channel 108 is narrow and generally linear in configuration and is preferably rectangular as shown at cross section 5-5 and 6-6 as seen in FIGS. 4-6. Other cross-sectional configurations, such as arcuate, are also contemplated by this disclosure. In order to reduce the volume of the fluid sample required for analysis to no more than roughly 30 μl, the upper fluid channel must be very narrow. Cross section 5-5 also details the through hole 138 that leads from the upper fluid channel 108 to the exit point 140 on the lower chip which is discussed in greater detail below.

As seen in FIGS. 2 and 3 a second chip 152 is disposed beneath the separation panel 104. In a preferred embodiment, the chip 152 is comprised of all amperometric sensors; however, a combination of amperometric, potentiometric and other sensor options placed upon the chip 152 are also contemplated with this disclosure. The discussion below is directed to a chip comprised solely of amperometric sensors; however, this characterization should not be considered limiting. Amperometric methods measure the electrical current flow produced from oxidation-reduction reactions. Types of amperometry include enzyme electrodes, such as the glucose oxidase method and the Clark $pO_2$ electrode. These types of designs are well known as biosensors and are adaptable for testing in the clinical laboratory as well as for point of care testing.

Enzyme-based biosensor technology was first developed to measure blood glucose. A solution of glucose oxidase is placed between the gas permeable membrane of the $pO_2$ electrode and an outer membrane that is semipermeable. Glucose in the blood diffuses through the semipermeable membrane and reacts with the glucose oxidase. Glucose is converted by glucose oxidase to hydrogen peroxide and gluconic acid.

A polarizing voltage is applied to the electrode, which oxidizes the hydrogen peroxide and contributes to the loss of electrons. Oxygen is consumed near the surface of the $pO_2$ electrode and its rate of consumption is measured. The loss of electrons and rate of decrease of $pO_2$ is directly proportional to the glucose concentration in the sample. The basic principles of operation for laboratory fluid analyzers are the same as for the previously described electrodes for pH, $pCO_2$, and $pO_2$; and ion specific electrodes for the measurement of electrolytes.

As seen in FIGS. 2 and 3, the amperometric chip 152 includes at least one analyte sensor 154 disposed over the lower fluid channel 112 and two electrical contact points 156, 158 for connecting the analyte sensor 154 with an analyzer (not shown). As seen in FIG. 3, positioned above the amperometric chip 152 is the separation panel 104. The separation panel 104 includes a lower surface 110 with a lower fluid channel 112 for passage of the sample fluid. As seen in FIG. 3, the separation panel 104 includes a lower surface 110 with a lower fluid channel 112, in fluid communication with the upper fluid channel 108. Optionally disposed between the amperometric chip 152 and the separation panel 104 is a lower gasket 160. The lower gasket 160 seals the separation panel 104 against leakage of the sample fluid and is preferably comprised of flexible fluid resistant material capable of forming a seal against leakage. The gasket 160 includes a cutout area 162 that coincides with the location and configuration of the lower fluid channel 112.

As seen in FIG. 3, the separation panel 104 also includes a pair of optional adjacent channels 164, 166 that straddle the lower fluid channel 112. These channels may facilitate the fabrication of the separation panel 104 by inhibiting warping that may otherwise result from excess molded material. The amperometric chip 152 is positioned beneath the separation panel 104 and includes, as shown in FIG. 2, at least one analyte sensor 154, and preferably many more, are positioned beneath the lower fluid channel 112. Each analyte sensor 154 includes two electrical contact points 156, 158 for connecting each analyte sensor 154 with an analyzer (not shown).

The lower fluid channel 112 serves as a conduit for the fluid being analyzed by at least one lower analyte sensor 154. This fluid channel 112 is narrow and generally linear in configuration and may be viewed at cross sections 5-5 and 6-6 as seen in FIGS. 5-6. In order to reduce the volume of the fluid sample required for analysis to no more than about 30 μl, the lower fluid channel 112, just like the upper fluid channel 108, must be very narrow. For example, at cross section 5-5, as shown in FIG. 5, the lower fluid channel 112 has a very narrow rectangular profile. Cross section 5-5 also details the through hole 138 that leads from the upper fluid channel 108 to the exit point 140 on the amperometric chip which is discussed in greater detail below.

Figure 7:
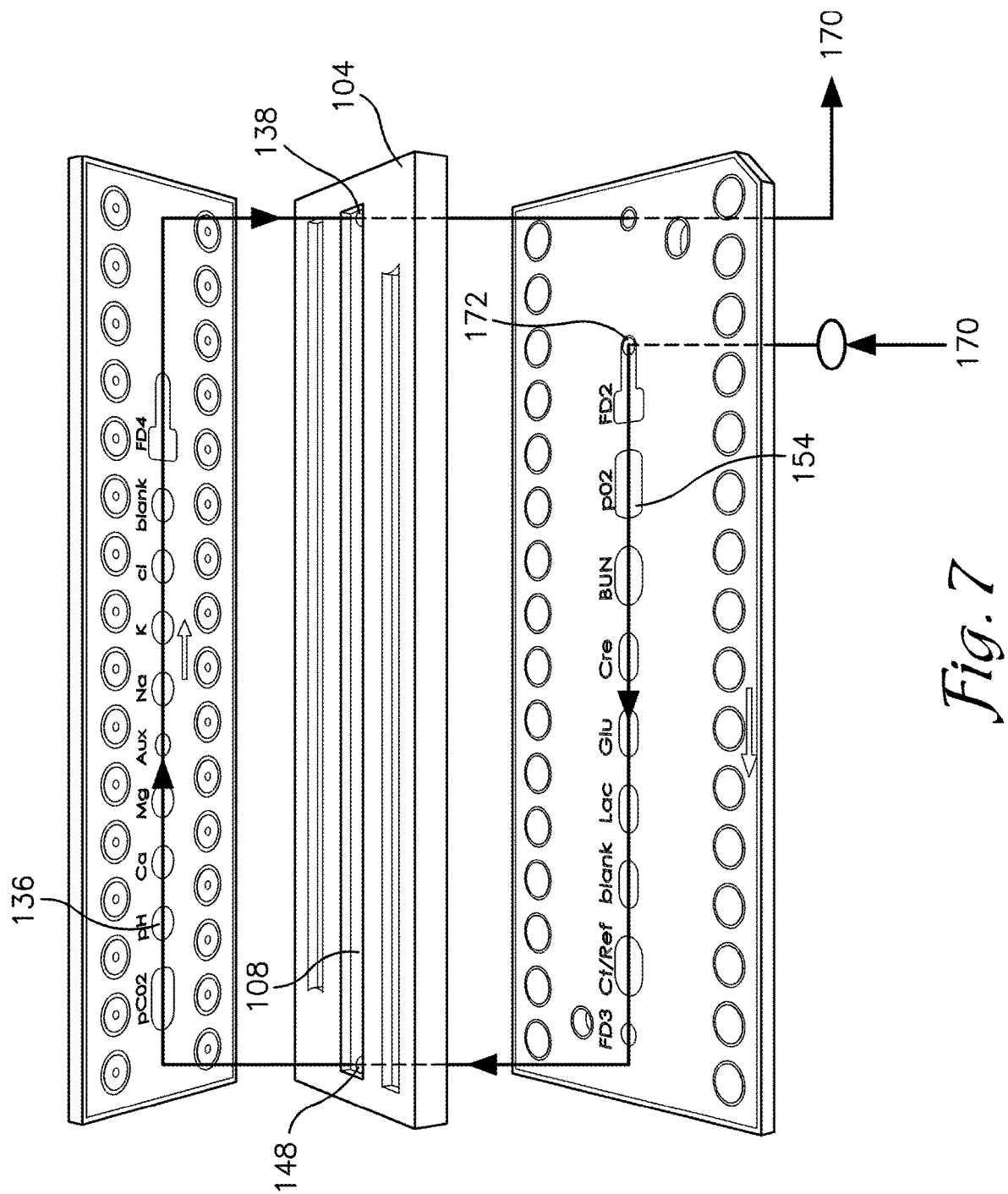
FIG. 7 is an exploded view of the potentiometric chip, separation panel and amperometric chip.
Figure 8:
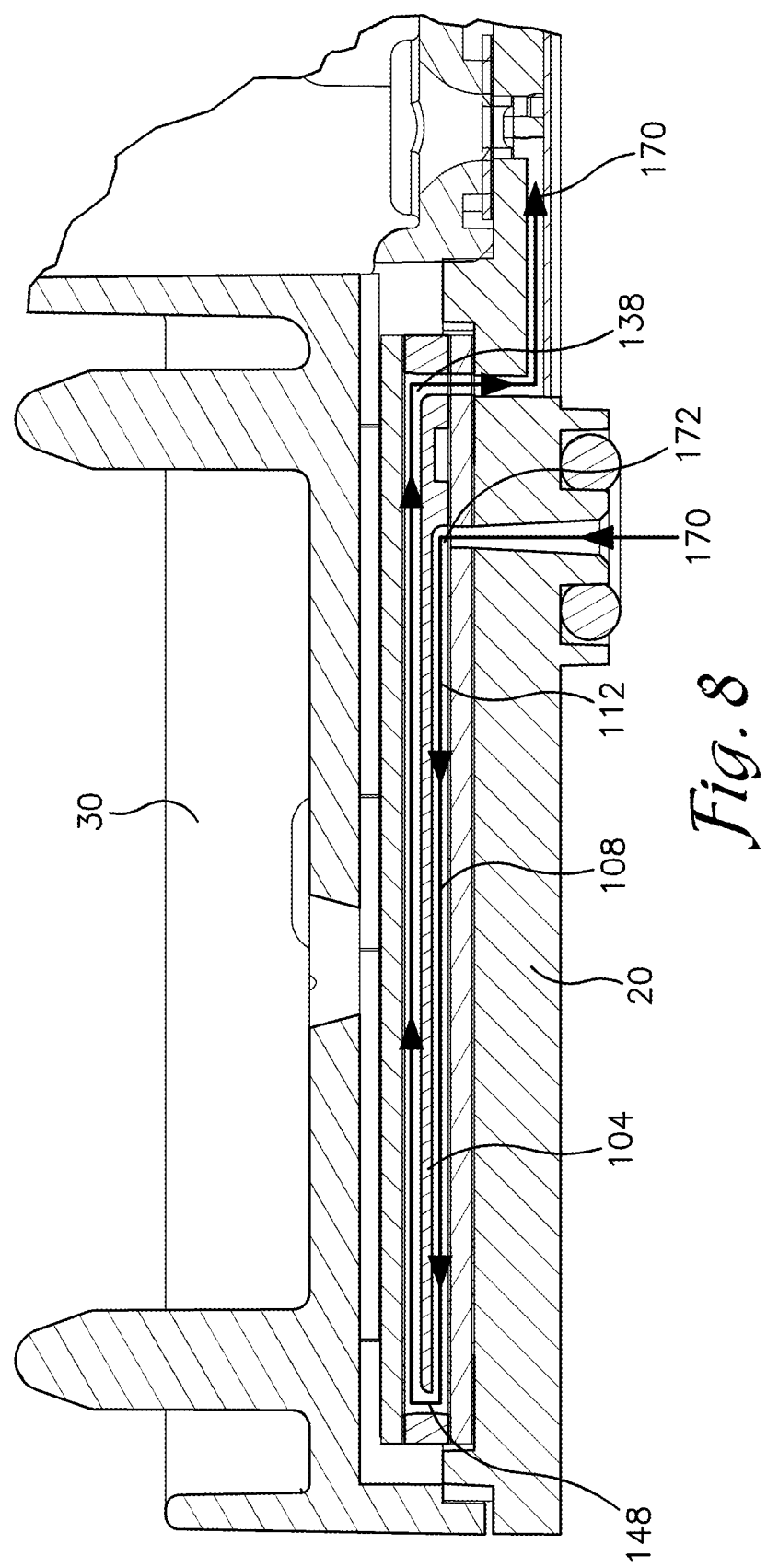
FIG. 8 is a cross sectional view of the fully assembled cartridge with sensor assembly installed therein.

Fluid 170 undergoing analysis enters the channel 112, as best seen in FIGS. 7 and 8 at the far extent of the channel through an opening 172. The fluid 170 then travels along the lower fluid channel 112 providing access to one or more amperometric analyte sensors 154. The fluid sample 170 then traverses through an opening 148 in the separation panel prior to entering the upper fluid channel 108. After entering the upper fluid channel 108 the fluid sample 170 traverses beneath at least one analyte sensor 136 prior to transiting through the exit opening 138 in the separation panel 104. FIG. 8 reveals a cross section view of the overall cartridge assembly 40 and details the fluid path through the sensor assembly 10.

Figure 9:
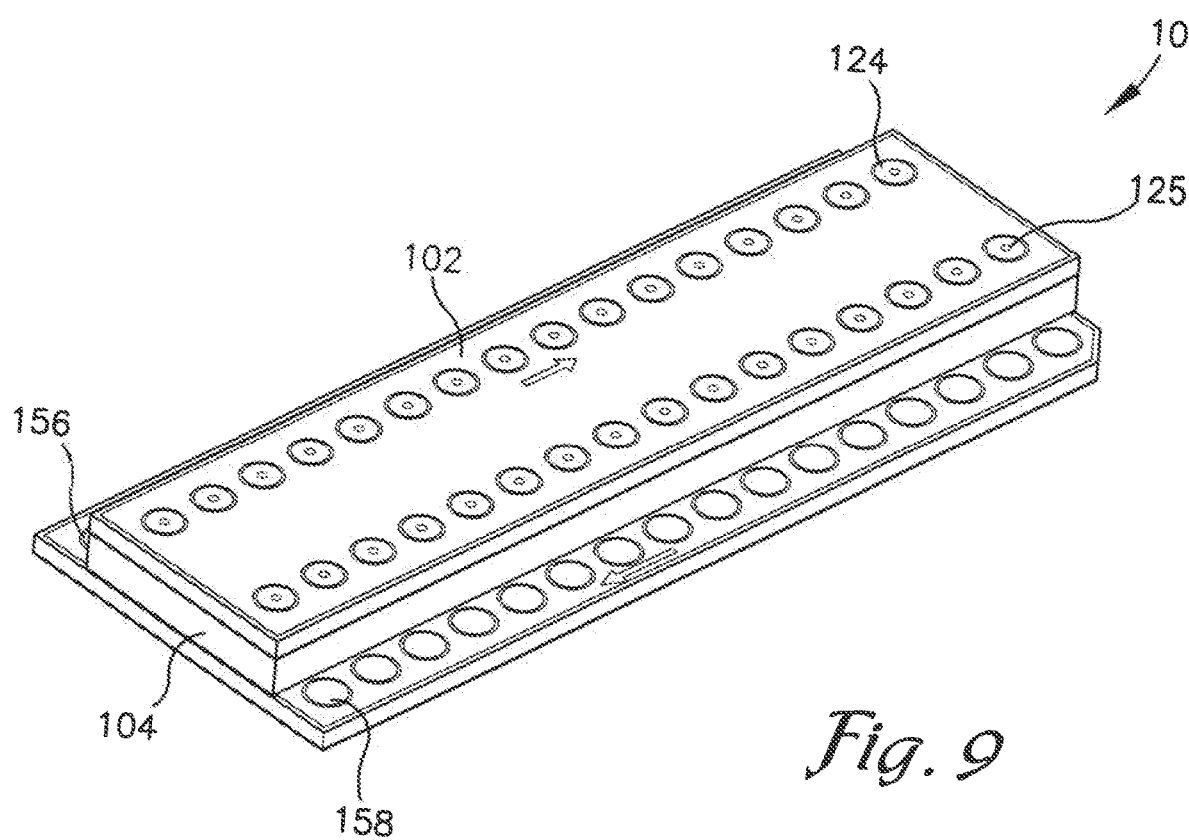
FIG. 9 is a perspective view of a fully assembled fluid sensor assembly.

As shown in FIG. 9, the sensor assembly 10 when fully assembled reveals analyte sensor contacts 124, 125 156, 158. These sensor contacts feed electrical signals to contact points located on the analyzer (not shown) where the voltage and current levels from each analyte sensor are separately analyzed. Following analysis, the pertinent details regarding the fluid analytes are reported out to the user to effectuate a diagnostic assessment.

Many different arrangements of the various components depicted, as well as components not shown, are possible without departing from the spirit and scope of the disclosed technology. Embodiments of the disclosed technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosed technology.

It will be understood that certain features and sub combinations are of utility and may be employed without reference to other features and sub combinations and are contemplated within the scope of the claims. Not all steps listed in the various figures need be carried out in the specific order described.

I claim:

1. A sensor assembly for analysis of physical parameters and chemical constituents of small volume samples of bodily fluids with at least two analyte sensors comprising:
    a separation panel, the separation panel further comprising an upper surface with an upper fluid channel for passage there through of the sample volume as well as a lower surface with a lower fluid channel in fluid communication with the upper fluid channel;
    a first chip disposed atop the separation panel, the first chip including at least one analyte sensor disposed over the upper fluid channel and one or more electrical contact points for connecting the analyte sensor with an analyzer; and
    a second chip disposed beneath the separation panel, the second chip including at least one analyte sensor disposed over the lower fluid channel and one or more electrical contact points for connecting the analyte sensor with an analyzer;
    wherein a bodily fluid sample traverses through the entire extent of the upper and lower fluid channels in fluid communication with the analyte sensors of the first and second chips.

2. The sensor assembly of claim 1, wherein the separation panel comprises first and second longitudinally disposed ends.

3. The sensor assembly of claim 2, wherein the upper and lower fluid channels span between the first and second longitudinally disposed ends.

4. The sensor assembly of claim 1, wherein the upper and lower fluid channels further comprise a first wall and a second wall.

5. The sensor assembly of claim 4, wherein the first and second walls of the upper and lower fluid channels are separated by a distance in a range of from 0.200 to 1.000 mm.

6. The sensor assembly of claim 1, wherein the sensor assembly has an inlet port configured for fluid communication with the lower fluid channel.

7. The sensor assembly of claim 1, wherein the sensor assembly has a fluid outlet in fluid communication with the upper fluid channel.

8. The sensor assembly of claim 1, wherein the separation panel is fabricated from an engineered plastic.

9. The sensor assembly of claim 1, wherein a total combined volume of the upper and lower fluid channels is in a range of from 30 μl to 40 μl.

10. The sensor assembly of claim 1, wherein a thickness of the separation panel is in a range of from 1.0 to 3.0 mm.

11. The sensor assembly of claim 1, wherein the at least one analyte sensor in each of the first and second chips is at least two adjacent analyte sensors.

12. The sensor assembly of claim 11, wherein the at least two adjacent sensor's are separated from each other by a distance in a range of from 0.200 to 2.000 mm.

13. The sensor assembly of claim 1, wherein the analyte sensors of the first chip are potentiometric sensors.

14. The sensor assembly of claim 1, wherein the analyte sensors of the second chip are amperometric sensors.

15. The sensor assembly of claim 1, wherein the upper and lower fluid channels are rectangular in cross-section.

16. The sensor assembly of claim 15, wherein the upper and lower fluid channels are arcuate in cross-section in proximity to a through hole leading from the lower to the upper fluid channel.

17. A sensor assembly for analysis of physical parameters and chemical constituents of small volume samples of bodily fluids with at least two analyte sensors comprising:
    a separation panel with an upper surface and a lower surface, the separation panel further comprising first and second longitudinally disposed ends with upper and lower fluid channels disposed within the upper and lower surfaces, respectively, and extending between the first and second longitudinally disposed ends and when in an operating mode bodily fluid is in fluid communication with both the upper and lower fluid channels;
    a first chip positioned atop the separation panel with at least one analyte sensor positioned over the upper fluid channel and when the sensor assembly is in an operating mode the bodily fluid is in fluid communication with the at least one analyte sensor; and a second chip positioned beneath the separation channel with at least one analyte sensor positioned beneath the lower fluid channel and when the sensor assembly is in an operating mode the bodily fluid is in fluid communication with the at least one analyte sensor, wherein the bodily fluid sample traverses through the entire extent of the upper and lower fluid channels in fluid communication with the analyte sensors of the first and second chips.

18. The sensor assembly of claim 17, wherein the upper and lower fluid channels in the upper and lower surfaces of the separation panel are arcuate in cross-section.

19. The sensor assembly of claim 17, wherein the upper and lower fluid channels in the upper and lower surfaces of the separation panel are rectangular in cross-section.

20. The sensor assembly of claim 17, wherein the upper and lower fluid channels are linear along the entire span of said channels.

21. The sensor assembly of claim 17, wherein a first gasket is positioned between the first chip and the separation panel to prevent leakage of the bodily fluid sample.

22. The sensor assembly of claim 17, wherein a second gasket is positioned between the second chip and the separation panel to prevent leakage of the bodily fluid sample.

* * * * *